(12) United States Patent
Fujikura

(10) Patent No.: US 8,404,467 B2
(45) Date of Patent: Mar. 26, 2013

(54) PROCESS FOR PRODUCING ANTIAGING AGENT, VULCANIZATION ACCELERATOR OR MODIFIED NATURAL RUBBER BY MEANS OF MICROORGANISM

(75) Inventor: Keitaro Fujikura, Kobe (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 572 days.

(21) Appl. No.: 12/078,266

(22) Filed: Mar. 28, 2008

(65) Prior Publication Data

US 2008/0242823 A1    Oct. 2, 2008

(30) Foreign Application Priority Data

Mar. 30, 2007    (JP) ................................. 2007-094749

(51) Int. Cl.
*C12P 7/40* (2006.01)
(52) U.S. Cl. .................................. 435/170; 435/252.35
(58) Field of Classification Search .................. 435/170, 435/252.35
See application file for complete search history.

(56) References Cited

U.S. PATENT DOCUMENTS

| 7,183,096 B2 | 2/2007 | Bloom et al. |
| 2006/0128001 A1 | 6/2006 | Yukawa et al. |

FOREIGN PATENT DOCUMENTS

| GB | 2 163 752 A | 3/1986 |
| JP | 60-222448 A | 11/1995 |
| JP | 2005-139239 A | 6/2005 |
| JP | 2006-152171 A | 6/2006 |
| RU | 2071487 C1 | 1/1997 |
| RU | 2235718 C2 | 9/2004 |
| WO | WO 00/59862 A2 | 10/2000 |

OTHER PUBLICATIONS

Szmant 1989. Organic Building Blocks of the Chemical Industry, Aniline section, pp. 548-574.*
NIA 2008. Can we prevent aging? Tips from the National Institute on Aging, pp. 1-8.*
Humphrey and Deidoerfer, 1960. 1960 Fermentation process review. Microbiological Process Report, pp. 359-385.*
Huang and Tang, 2007. Bioprocessing for value-added products from renewable resources; New technologies and applications, Chpater 8—Bacterial and yeastt cultures—process characteristics, products, and applications, pp. 185-223.*
Deidoerfer et al, 1961. 1961 Fermentation process report. Microbiological Process Report, pp. 273-303.*
Zissi and Lyberatos, 2000. Biodegradation of p-aminobenzene by *Bacillus subtillis* under aerobic conditions. Journal of Industrial Microbiology and Biotechnology, vol. 19:49-55; as provided by applicant in the Aug. 6, 2008 IDS.*
Draths et al, 1992. Biocatalysis and nineteenth century organic chemistry: conversion of D-glucose into Quinoid organics. J. Am. Chem. Soc., vol. 114:9725-9726.*
Zissi et al., "Biodegradation of p-aminoazobenzene by *Bacillus subtilis* under aerobic conditions," Journal of Industrial Microbiology & Biotechnology, vol. 19, pp. 49-55, (1997), XP002485000.
Full machine English translation of JP 2006-152171-A, published on Jun. 15, 2006.
Full English translation of JP 2005-139239-A, published on Jun. 2, 2005.

* cited by examiner

*Primary Examiner* — Ruth Davis
(74) *Attorney, Agent, or Firm* — Birch, Stewart, Kolasch & Birch, LLP

(57) ABSTRACT

The object of the present invention is to provide processes for producing an antiaging agent, a vulcanization accelerator and a modified natural rubber, which are environmentally friendly and allow to make provision against a decrease of petroleum resources in the future. According to the present invention, glucose is used as carbon neutral resources and is converted into aniline or an aniline derivative by a microorganism. An antiaging agent, a vulcanization accelerator or a modified natural rubber is produced from thus obtained aniline or aniline derivative.

7 Claims, No Drawings

PROCESS FOR PRODUCING ANTIAGING AGENT, VULCANIZATION ACCELERATOR OR MODIFIED NATURAL RUBBER BY MEANS OF MICROORGANISM

TECHNICAL FIELD

The present invention relates to a process for producing an antiaging agent, a vulcanization accelerator or a modified natural rubber by means of a microorganism. More particularly, the present invention relates to a process for producing an antiaging agent, a vulcanization accelerator or a modified natural rubber by using aniline or an aniline derivative produced by a microorganism.

BACKGROUND ART

At present, antiaging agents used for a rubber, thiazole vulcanization accelerators and sulfenamide vulcanization accelerators are synthesized from aniline which is produced from petroleum as a raw material. Assuming a rise in oil prices and exhaustion of oil, a production process which does not use oil is desired. Further, processes of production of antiaging agents and vulcanization accelerators cause global warming since industrial production of aniline from petroleum resources emit a large amount of heat and carbon dioxide. Therefore, based on an idea of utilizing natural resources, a method is known wherein a vulcanization accelerator is synthesized by the use of a naturally-derived long-chain amine, as a material, which is obtained by reductive amination of a saturated or unsaturated fatty acid which is obtained by hydrolysis of a natural fat and oil (JP-A-2005-139239).

However, acrylonitrile, mercaptobenzothiazoles and dibenzothiazolyl disulfide are used in the process of producing vulcanization accelerators. There is no description that these materials are produced from natural resources.

Further, a production process is known wherein a modified natural rubber is produced by a graft polymerization or an addition of a compound containing a polar group under mechanical shear stress to a natural rubber raw material (JP-A-2006-152171). However, it is not assumed that a naturally-derived material is used as a compound containing a polar group.

SUMMARY OF THE INVENTION

It is an object of the present invention to provide processes for producing an antiaging agent, a vulcanization accelerator and a modified natural rubber, which are environmentally friendly and allow to make provision against a decrease of petroleum resources in the future.

The present invention relates to a process for producing an antiaging agent which comprises converting glucose into aniline or an aniline derivative by a microorganism.

Further, the present invention relates to a process for producing a vulcanization accelerator which comprises converting glucose into aniline or an aniline derivative by a microorganism.

Furthermore, the present invention relates to a process for producing a modified natural rubber which comprises converting glucose into aniline or an aniline derivative by a microorganism and modifying a natural rubber by said aniline or aniline derivative.

DETAILED DESCRIPTION OF THE INVENTION

In the following, the present invention is described in detail.

In the present invention, glucose is used as carbon neutral resources and is converted into aniline or an aniline derivative by a microorganism. An antiaging agent, a vulcanization accelerator or a modified natural rubber is produced from thus obtained aniline or aniline derivative.

Glucose used in the present invention is obtained from plants which take in carbon dioxide in the atmosphere. The examples thereof may include waste wood, paddy straw, weed and non-edible part of food crop (stem, root and xylem). Glucose can be obtained by adding an acid to the materials and hydrolyzing them or carrying out a hot-compressed water treatment.

Then a nitrate salt which is obtained by a hot water extraction of a plant is added to the glucose and the mixture is converted into aniline or an aniline derivative by a microorganism.

Examples of the microorganism used in the present invention may include *Escherichia coli* W strain (ATCC9637) and actinomycetes such as *Streptomyces griseus* (ATCC23345 and ATCC23921).

Conversion of glucose into aniline can be carried out in water or a solvent which is a mixture of water and an organic solvent. Examples of the organic solvent may include methanol, ethanol, dimethyl sulfoxide, diethyl ether, tetrahydrofuran and acetone.

Temperature for conversion is preferably 20° C. to 42° C. If the temperature is below 20° C., activity of the microorganism is depressed. If the temperature is above 42° C., the microorganism tends to be killed. Therefore, in both cases yield decreases. It is more preferable that the lower limit is 25° C. and the upper limit is 30° C.

It is preferable that pH is between 4 and 9 during the reaction. If pH is not within the above range, aniline production efficiency drops extremely.

Cultivation time is 3 to 6 days, preferably 4 to 5 days.

Examples of aniline derivative may include compounds which have a substituent such as hydroxyl group or carboxyl group on the benzene ring of aniline. Preferable aniline derivatives include 3-carboxy-6-hydroxyaniline.

Examples of antiaging agent may include N-(1,3-dimethylbutyl)-N'-phenyl-p-phenylenediamine as p-phenylenediamine antiaging agent, and polymer of 2,2,4-trymethyl-1,2-dihydroquinoline as quinoline antiaging agent.

For example, N-(1,3-dimethylbutyl)-N'-phenyl-p-phenylenediamine can be produced from aniline by the following synthesis approach. Here, methyl isobutyl ketone which is added to the amine, an intermediate, can be synthesized by dry distillation of calcium acetate or aldol condensation of acetone which is obtained by acetone-buthanol fermentation. These methods allow to produce the compound without petroleum resources.

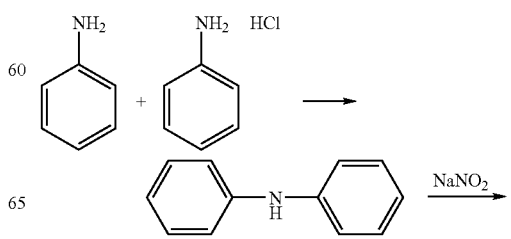

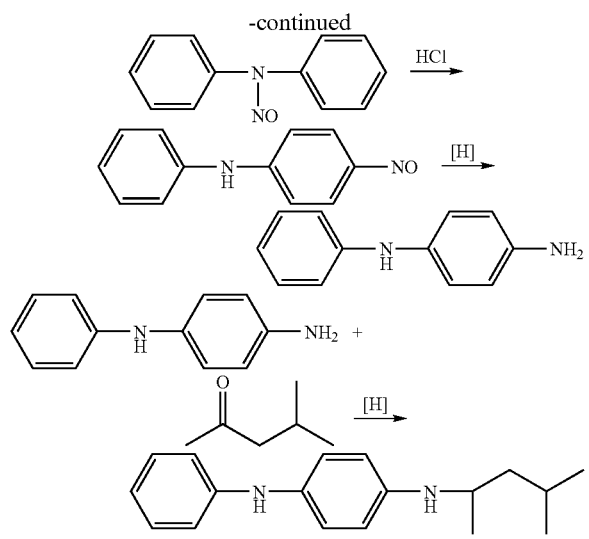

Polymer of 2,2,4-trimethyl-1,2-dihydroquinoline can be produced from aniline by continually supplying acetone as needed at 140° C. in the presence of an acidic catalyst. The method allows to produce the compound without petroleum resources.

Examples of vulcanization accelerator may include 2-mercaptobenzothiazole and dibenzothiazyl disulfide as thiazole vulcanization accelerators, and N-cyclohexyl-2-benzothiazyl sulfenamide, N,N-dicyclohexyl-2-benzothiazyl sulfenamide, and N-tert-butyl-2-benzothiazyl sulfenamide as sulfenamide vulcanization accelerators.

2-Mercaptobenzothiazole can be produced from aniline by the following synthesis approach. Here, carbon disulfide can be generated and separated for example by reacting mustard oil, which is contained about 0.4% in leaf mustard, with hydrogen sulfide. The method allows to produce the vulcanization accelerator without petroleum resources. Dibenzothiazyl disulfide is synthesized by oxidizing thus produced 2-mercaptobenzothiazole.

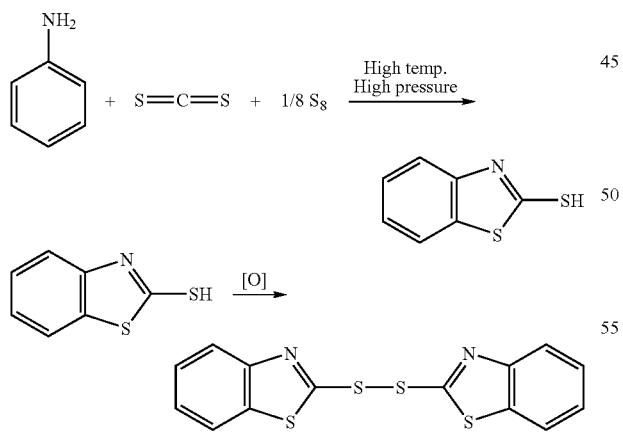

As a natural rubber, deproteinized natural rubber can be used as well as normal natural rubber. Modified natural rubber can be produced by graft polymerization of aniline and natural rubber under electron beam irradiation, mechanical shear stress and the like.

The antiaging agents, vulcanization accelerators or modified natural rubbers, which are obtained by the production process of the present invention, can be used as materials for normal rubber products, and are especially useful as rubber compositions used for tires.

The rubber composition can be produced by mixing inorganic fillers such as clay, aluminum hydroxide and calcium carbonate, and compounding agents which are used in ordinary rubber industry such as process oil, softeners, antiaging agents, vulcanization agents and vulcanization aids as needed as well as rubber components, silica, silane coupling agents, carbon black and vulcanization accelerators.

The rubber composition is produced by kneading rubber components and necessary compounding agents with a rubber kneading machine such as a bunbury mixer or an open roll, kneading various additives if necessary, extruding thus obtained unvulcanized rubber composition into a form of respective tire parts, forming an unvulcanized tire on a tire molding machine, and hot pressing the unvulcanized tire in a vulcanizer.

According to the present invention, an antiaging agent, a vulcanization accelerator or a modified natural rubber is produced from aniline or an aniline derivative obtained by the use of a microorganism. The process is environmentally friendly and allows to make provision against a decrease of petroleum resources in the future.

BEST MODES FOR CARRYING OUT THE INVENTION

The following examples illustrate the present invention concretely. They, however, do not limit the scope of the present invention.

EXAMPLES

Example of Production of Aniline Using a Microorganism

As a starting material, glucose was controlled to have a concentration of 5%. TSB (Trypticase Soy Broth) culture medium was heat-treated at 120° C. for 20 minutes and cooled to room temperature. *Streptomyces griseus* (ATCC23345 and ATCC23921) was cultured at 28° C., 170 rpm, for 4 to 5 days under aerobic condition in the culture medium. Diethylether was then added to the culture medium and extraction was carried out twice. A crude extract was concentrated by an evaporator and purified by flash chromatography using a column filled with silica gel 60. Aniline was identified by NMR and IR.

Example of Production of Antiaging Agent from Aniline

To a flask equipped with an acetone introduction apparatus, a distillation apparatus, a thermometer and an agitator were added 190 g (1.5 mol) of aniline which was obtained by chemical conversion by means of a microorganism and hydrochloric acid (0.20 mol) as an acidic catalyst, and then heated to 140° C. The reaction system was kept at 140° C., and 580 g (10 mol) of acetone was continuously supplied to the reaction system for 6 hours. Distilled unreacted acetone and aniline were returned to the reaction system occasionally. As a result, 180.7 g (yield: about 30%) of polymer of 2,2,4-trimethyl-1,2-dihydroquinoline was obtained. Its degree of polymerization is 2 to 4. Unreacted aniline and monomer of 2,2,4-trimethyl-1,2-dihydroquinoline were recovered by distillation under reduced pressure. Unreacted aniline distilled at 140° C., and the monomer distilled after the temperature was raised to 190° C. Yield of the monomer was 19.1 g (6.9%).

The invention claimed is:

1. A process for producing an antiaging agent for a rubber product, comprising the steps of:
   (a) converting glucose into aniline or 3-carboxy-6-hydroxyaniline by *Escherichia coli* or *Streptomyces griseus*; and
   (b) reacting the aniline or the 3-carboxy-6-hydroxyaniline converted in step (a) with a ketone in the presence of an acidic catalyst to produce the antiagent agent.

2. A process for producing a vulcanization accelerator, comprising the steps of:
   (a) converting glucose into aniline or 3-carboxy-6-hydroxyaniline by *Escherichia coli* or *Streptomyces griseus*; and
   (b) reacting the aniline or the 3-carboxy-6-hydroxyaniline converted in step (a) with carbon disulfide to produce the vulcanization accelerator.

3. A process for producing a modified natural rubber, comprising the steps of:
   (a) converting glucose into aniline or 3-carboxy-6-hydroxyaniline by *Escherichia coli* or *Streptomyces griseus*; and
   (b) graft polymerizing the aniline or the 3-carboxy-6-hydroxyaniline converted in step (a) on a natural rubber to produce the modified natural rubber.

4. The process for producing an antiaging agent according to claim 1, wherein the antiaging agent is a p-phenylenediamine antiaging agent or a quinoline antiaging agent.

5. The process for producing a vulcanization accelerator according to claim 2, wherein the vulcanization accelerator is a thiazole vulcanization accelerator or a sulfenamide vulcanization accelerator.

6. The process for producing an antiaging agent according to claim 1, wherein the ketone is acetone or methyl isobutyl ketone.

7. The process for producing an antiaging agent according to claim 1, wherein the acidic catalyst is hydrochloric acid.

* * * * *